(12) United States Patent
Shirkhodaie et al.

(10) Patent No.: US 8,746,924 B2
(45) Date of Patent: Jun. 10, 2014

(54) ILLUMINATION SYSTEM WITH ILLUMINATION SHIELD

(75) Inventors: Amir Shirkhodaie, Nashville, TN (US); Robert Moriarty, Greenwood, IN (US); Kong Ma, Carmel, IN (US)

(73) Assignee: Rolls-Royce Corporation, Indianapolis, IN (US)

( * ) Notice: Subject to any disclaimer, the term of this patent is extended or adjusted under 35 U.S.C. 154(b) by 111 days.

(21) Appl. No.: 13/416,770

(22) Filed: Mar. 9, 2012

(65) Prior Publication Data

US 2012/0236557 A1 Sep. 20, 2012

Related U.S. Application Data

(60) Provisional application No. 61/450,963, filed on Mar. 9, 2011.

(51) Int. Cl.
*F21V 5/00* (2006.01)
(52) U.S. Cl.
USPC ............ 362/246; 362/235; 362/558; 362/317; 362/613; 362/234
(58) Field of Classification Search
USPC ............ 362/235, 246, 558, 317, 382, 296.01, 362/84, 298, 517, 613, 241, 234, 16
See application file for complete search history.

(56) References Cited

U.S. PATENT DOCUMENTS

| | | | |
|---|---|---|---|
| 4,454,542 A | 6/1984 | Miyazawa | |
| 5,051,872 A | 9/1991 | Anderson | |
| 5,604,550 A | 2/1997 | White | |
| 2002/0149943 A1* | 10/2002 | Obata | 362/339 |
| 2007/0090193 A1* | 4/2007 | Nunnink et al. | 235/473 |
| 2008/0130280 A1 | 6/2008 | Rodstein et al. | |
| 2008/0170380 A1* | 7/2008 | Pastore | 362/16 |
| 2009/0310827 A1* | 12/2009 | Einighammer et al. | 382/115 |
| 2010/0020539 A1 | 1/2010 | Nunnink | |
| 2010/0118530 A1* | 5/2010 | Nagai | 362/235 |

OTHER PUBLICATIONS

International Search Report and Written Opinion, ISA/US, PCT/US2012/028543, Rolls-Royce Corporation Jul. 5, 2012.

* cited by examiner

*Primary Examiner* — Britt D Hanley
*Assistant Examiner* — Kevin Quarterman
(74) *Attorney, Agent, or Firm* — Krieg DeVault LLP

(57) ABSTRACT

An apparatus for an illumination system including a concentric light source providing a quantity of light; a diffusion shield to diffuse the light and produce a diffused illumination where the diffused illumination is provided to a component positioned in an interior portion of the diffusion shield; a support structure where the diffusion shield is mechanically coupled with the support structure at a first base portion of the diffusion shield and where the concentric light sources are mechanically coupled with the support structure and positioned radially outward from the first base portion of the diffusion shield; and a harvesting shield where the harvesting shield is mechanically coupled with the support structure and positioned radially outward from the concentric light sources and where the harvesting shield redirects at least a portion of the quantity of light from the concentric light sources towards the diffusion shield.

15 Claims, 3 Drawing Sheets

ILLUMINATION SYSTEM WITH ILLUMINATION SHIELD

CROSS REFERENCE TO RELATED APPLICATIONS

The present application claims the benefit of U.S. Provisional Patent Application 61/450,963, filed Mar. 9, 2011, and is incorporated herein by reference. This application also incorporates by reference, in their entirety, the following concurrently filed applications: INTELLIGENT AIRFOIL COMPONENT SURFACE IMAGING INSPECTION, Ser. No. 13/416,315; INTELLIGENT AIRFOIL COMPONENT GRAIN DEFECT INSPECTION, Ser. No. 13/416,516; INTELLIGENT AIRFOIL COMPONENT SURFACE INSPECTION, Ser. No. 13,416,409; AUTOMATED OBJECT MANIPULATION SYSTEM, Ser. No. 13,416,705; and PROTOCOL-BASED INSPECTION SYSTEM, Ser. No. 13,416,610.

TECHNICAL FIELD

The present invention generally relates to illumination systems, and more particularly, but not exclusively, to a continuous diffuse illumination system.

BACKGROUND

Present approaches to illumination systems used in the inspection of parts, such as the inspection of gas turbine engine parts, suffer from a variety of drawbacks, limitations, disadvantages and problems including those respecting glare and others. There is a need for the unique and inventive diffuse illumination apparatuses, systems and methods disclosed herein.

SUMMARY

One embodiment of the present invention is a unique object illumination system. Other embodiments include apparatuses, systems, devices, hardware, methods, and combinations for a continuous diffuse illumination system for an inspection system. Further embodiments, forms, features, aspects, benefits, and advantages of the present application shall become apparent from the description and figures provided herewith.

DETAILED DESCRIPTION OF THE ILLUSTRATIVE EMBODIMENTS

Figure 1:
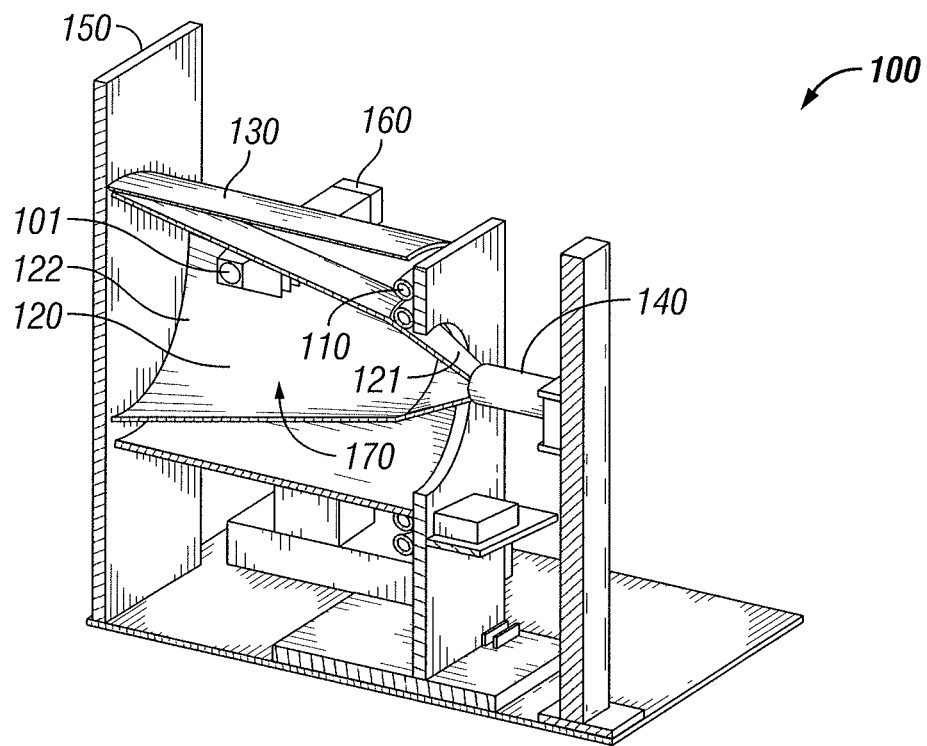
FIG. 1 is an illustration of an embodiment of an illumination system of the present application.

For the purposes of promoting an understanding of the principles of the invention, reference will now be made to the embodiments illustrated in the drawings and specific language will be used to describe the same. It will nevertheless be understood that no limitation of the scope of the invention is thereby intended. Any alterations and further modifications in the described embodiments, and any further applications of the principles of the invention as described herein are contemplated as would normally occur to one skilled in the art to which the invention relates.

With reference to FIG. 1, an object illumination system 100 of one embodiment of the present application is shown having a set of concentric fluorescent light bulbs 110, a diffusion shield 120 positioned radially inwards of concentric fluorescent light bulbs 110, and a cylindrical illumination harvesting shield 130 positioned radially outward from concentric fluorescent light bulbs 110. In this embodiment, an imaging system 140 is shown located to capture an image of a component 101 positioned within diffusion shield 120 by a manipulation system 160.

Concentric fluorescent light bulbs 110 can serve as the light source for object illumination system 100. In one embodiment, concentric fluorescent light bulbs 110 can include a single light or illumination source. In other embodiments, concentric fluorescent light bulbs 110 can include partial rings or configurations positioned in concentric circles or related arrangements. Illumination from concentric fluorescent light bulbs 110 can include fluorescent, incandescent, LED or other illumination as known in the art. Thus, as used herein, fluorescent light bulbs/sources used in any given embodiment can be replaced individually and/or collectively in other embodiments with other light bulbs/sources such as incandescent, LED, etc. Configurations and shapes other than rings or circles can, in some embodiments, be used for concentric fluorescent light bulbs 110 to provide illumination to the portions of a component presented to the imaging system. Illumination arrangements can be determined based on component parameters. Other forms of radiance can be applied where diffused light can illuminate an object and produce an image having a relatively balanced intensity of radiance. In further embodiments, multiple light sources within a single system can provide a variation of illumination arrangements which can be specified based on component parameters such as material, shape, and size to name a few. Further, longitudinal adjustment of the distance between the light source and the position of the component can allow control of the extent of illumination intensity provided to the component.

In another embodiment, diffusion shield 120 can have a truncated-type cone shape. Concentric fluorescent light bulbs 110 can be positioned radially outwards of a small radius base 121 of cone-shaped diffusion shield 120. The truncated cone-shape provides an opening for placing the detection portion of imaging system 140 at small radius base 121 of diffusion shield 120. In yet other embodiments, a background 150 is positioned at a large radius base 122 of cone-shaped diffusion shield 120. In one form the background 150 can be green.

Diffusion shield 120 can be composed of a material which allows penetration of bright illumination from a light source external to diffusion shield 120 to diffuse to the inside of a conic tunnel 170 of diffusion shield 120 where component 101 can be positioned for imaging purposes. In one form, the diffusion shield can be a plastic polymer material. Diffusion shield 120 is structured to diffuse light from concentric fluorescent light bulbs 110 as the light passes through diffusion shield 120 to illuminate the component.

A cylindrical illumination harvesting shield 130 is structured to redirect at least a portion of the light from concentric fluorescent light bulbs 110 to diffusion shield 120. Cylindrical illumination harvesting shield 130 is shown in this embodiment with a cylindrical shape. The shape of a harvesting shield can be structured to accommodate various selections of illumination arrangements, diffusion shields, and components, for example. A harvesting shield can be permanently placed in the system or can be removable to provide flexibility in an illumination system. The harvesting shield can be composed of various materials. In some embodiments, the material can be selected to provide a degree of redirection or reflectivity. Illumination harvesting shield 130 can be used to intensify and redirect ambient light through diffusion shield 120 to illuminate component 101.

In embodiments with imaging system 140 positioned in relation to diffusion shield 120 so as to produce an image of component 101, imaging system 140 can further include a camera utilizing a conventional light or other electromagnetic radiation type such as x-ray, ultraviolet, fluorescent and the like. In various embodiments, images taken of an object by imaging system 140 can be utilized for conducting an analysis of the component. The analysis can include component identification, defect determination, quality assessments and the like, some or all of which are associated with an inspection regime. For example, the embodiments disclosed herein can be used with an inspection regime that involves evaluating gas turbine engines and associated components as will have been appreciated by other aspects of the instant application. Such components can includes vanes, blades, etc. of the gas turbine engine.

An illumination system of one embodiment is structured to place an object at one end of an illumination tunnel created by a generally cone-shaped diffusion shield. An illumination source produces illumination which is diffused as it passes through the diffusion shield. The diffused light then illuminates the object. In a further embodiment, the object being illuminated can be positioned near a large radius base of the diffusion shield with a manipulation system. The manipulation system can include a robotic system, such as a multi-axis robotic system. Once the object is positioned, an imaging system such as a camera is capable of capturing perspective images of the object as the object is manipulated by the multi-axis robotic system. In one form, the imaging system can be attached at a small radius base of the cone-shaped diffusion shield. The imaging system is capable of capturing images of the object for further analysis.

In further embodiments, a multi-axis robotic system is capable of performing a series of controlled motions to expose different sections of a component to an imaging system producing at least one image of the component within a diffusion system. The diffusion system can include a diffusion shield and a harvesting shield. The diffusion shield can be structured to diffuse illumination from an illumination arrangement as the illumination passes through the diffusion shield. The harvesting shield can be structured to redirect at least a portion of the illumination from the illumination arrangement toward the diffusion shield.

In yet another embodiment, by longitudinal adjustment of the distance of a set of fluorescent light bulbs to the location where a component is positioned by a manipulation system, the extent of illumination intensity reaching the component can be controlled. Inside an illumination tunnel of a diffusion system, the component can be exposed to diffused lighting without any direct projection of a light source on the component, and hence a well-balanced intensity of illumination can be achieved. With diffused illumination, an imaging system can be capable of acquiring images of a light reflecting component without irregularities from reflections.

Figure 2:
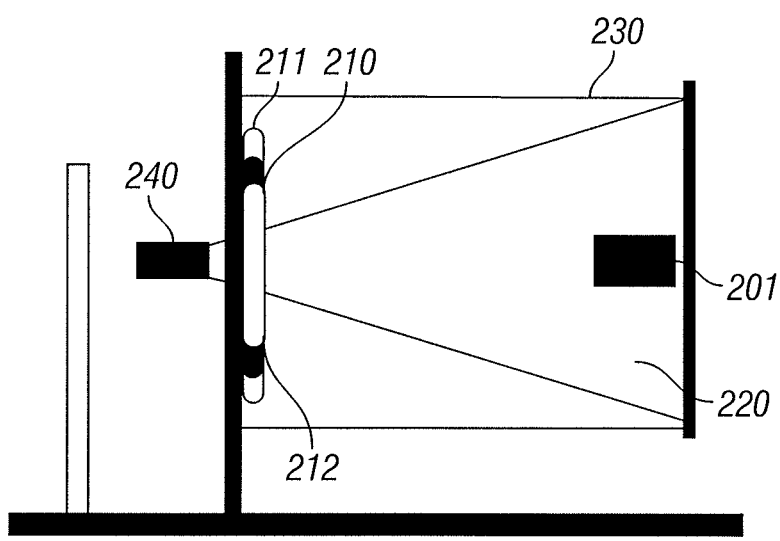
FIG. 2 is a diagram of an embodiment of the present application.

In another embodiment, an external illumination harvesting shield can be introduced to change the intensity and uniformity of supplied ambient illumination to an object. FIG. 2 is a cross-sectional schematic diagram illustrating the mechanics of an illumination harvesting shield 230 of one embodiment of the present application. Illumination harvesting shield 230 allows illumination produced from a florescent light source 210 to be redirected toward a cone-shaped diffusion shield 220 where an object 201 within the cone-shaped diffusion shield 220 can be exposed to an imaging system 240. In this embodiment, florescent light source 210 is shown as a first ring fluorescent light bulb 211 and a second ring florescent light bulb 212. Florescent light source 210 can have other shapes and configurations designed to meet the requirements of an inspection system including the object being inspected. Illumination harvesting shield 230 can be used to intensify and unify the ambient radiance from florescent light bulbs 211, 212 which can diffuse through cone-shaped diffusion shield 220 to illuminate object 201 positioned within the conic tunnel of cone-shaped diffusion shield 220.

Figure 3:
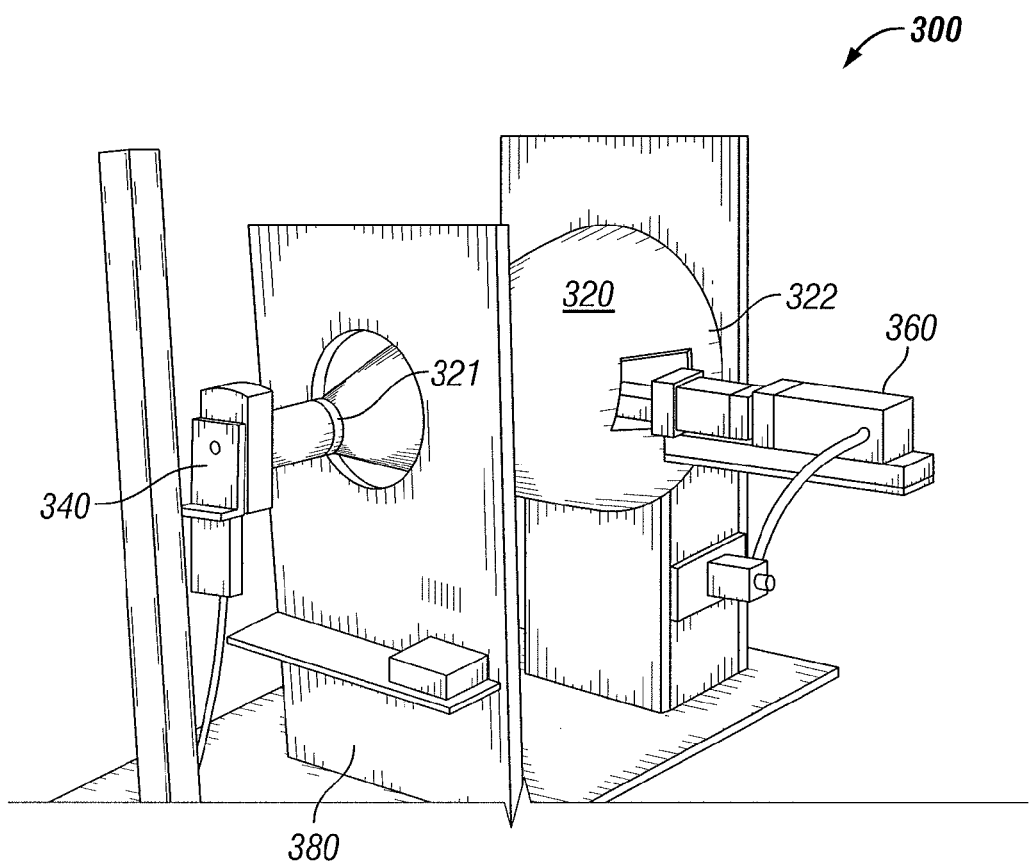
FIG. 3 is an arrangement of components for an embodiment of the present application.

FIG. 3 demonstrates an illumination system 300 having a cone-shaped diffusion shield 320 with a small radius base 321 and a large radius base 322. Illumination system 300 is also shown with a manipulation system 360 to position a component (not shown) within diffusion shield 320 to expose the component to an imaging system 340. Fluorescent lighting bulbs are present but not visible in FIG. 3 on the opposing side of an illumination support 380. An illumination harvesting shield can be used in the embodiment of FIG. 3 even though such a shield is not currently depicted.

An embodiment with a manipulation system 360 can include a robotic part manipulator and positioning algorithms to provide predetermined part presentation and positioning during an inspection process. Manipulator system 360 is capable of presenting a component in at least one position for imaging system 340. Manipulation system 360 can include various forms of component positioning equipment. In one embodiment, the manipulation system provides a single stationary position for the component.

Figure 4:
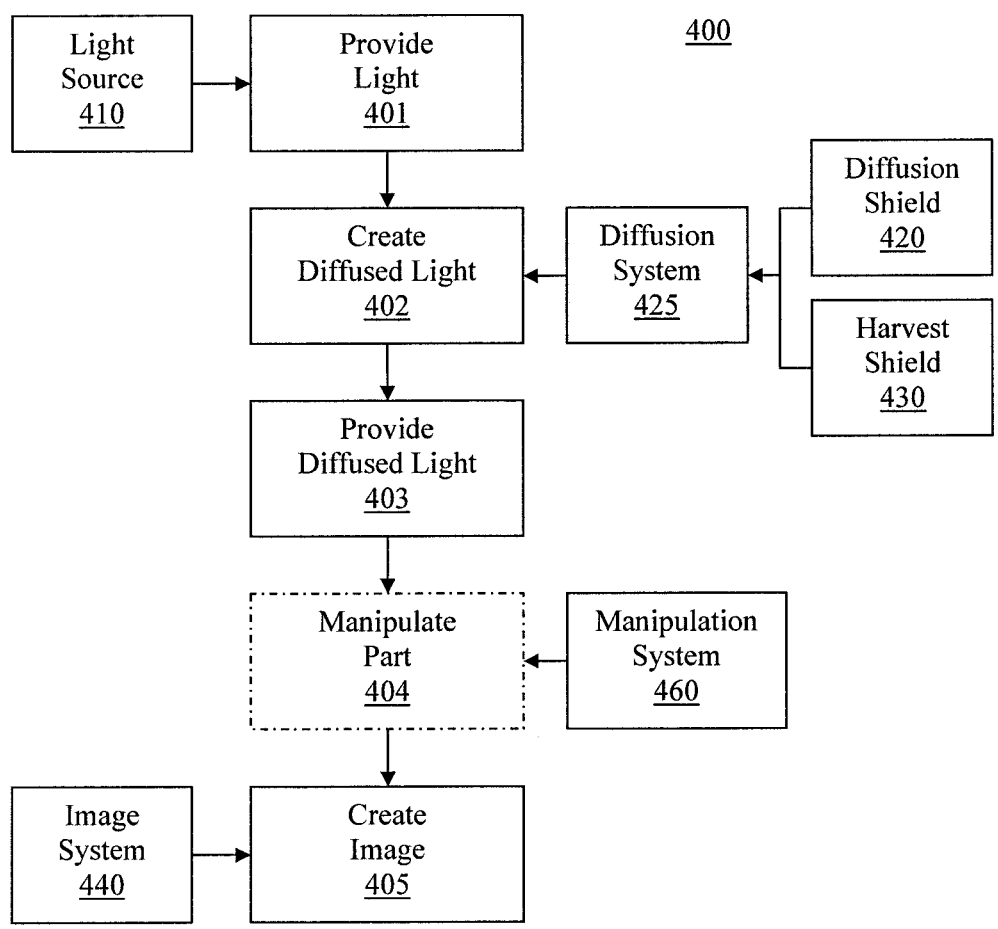
FIG. 4 is a process flow diagram of an embodiment of the present application.

FIG. 4 illustrates one embodiment of an illumination process 400 utilizing an illumination system. Operation 401 is shown initiating illumination process 400 and includes providing a source of illumination or light 410. In one embodiment, the source of light 410 can be from a set of concentric fluorescent light bulbs. Illumination process 400 continues with operation 402 which creates a diffused light. Operation 402 utilizes a diffusion system 425. Diffusion system 425 can include a diffusion shield 420 and a harvesting shield 430. Diffusion shield 420 can be structured to diffuse illumination from the source of illumination as the illumination passes through the diffusion shield. Harvesting shield 430 can be structured to redirect at least a portion of the illumination from the source of illumination toward the diffusion shield.

The diffused light produced in operation 402 is provided in order to illuminate an object in operation 403. An imaging system 440 is then able to create an image of the object illuminated by the diffused light from operation 403 in operation 405. Imaging system 440 can include a camera and image analysis. In an alternative, operation 404 can vary the position of the illuminated object during operation 403 and 405. Operation 404 can utilize an automated manipulation system 460.

One aspect of the present application is an apparatus including a set of concentric light sources capable of providing a quantity of light; and a diffusion shield structured to diffuse the quantity of light and produce a diffused illumination, said diffused illumination being provided to a component positioned in an interior portion of the diffusion shield.

Features of this aspect can include a support structure where the diffusion shield is mechanically coupled with the support structure at a first base portion of the diffusion shield and the set of concentric light sources are mechanically coupled with the support structure and positioned radially outward from the first base portion of the diffusion shield; a harvesting shield where the harvesting shield is mechanically coupled with the support structure and positioned radially outward from the set of concentric light sources and where the harvesting shield redirects at least a portion of the quantity of light from the set of concentric light sources towards the diffusion shield; an imaging system positioned at the first base portion of the diffusion shield and is capable of producing at least one image of the component; and a manipulation system capable of presenting the component to the imaging system within the diffusion shield and wherein the manipulation system is positioned approximate a second base portion of the diffusion shield.

Another aspect of this application is an apparatus including a florescent illumination arrangement and a system of shields where an object is substantially uniformly illuminated by the florescent illumination arrangement and the system of diffusion shields. Features of this aspect can include a quantity of illumination from the florescent illumination arrangement being diffused by the system of shields to produce a diffused quantity of illumination where the object is substantially uniformly illuminated by the diffused quantity of illumination; an imaging system positioned at a first base portion of the diffusion shield which is capable of producing at least one image of the object; and a manipulation system capable of presenting the object to the imaging system within the diffusion shield where the manipulation system is positioned approximate a second base portion of the diffusion shield.

Further features of this aspect can include the system of shields having a diffusion shield and a harvesting shield where the diffusion shield is structured to diffuse the quantity of illumination from the florescent illumination arrangement as the quantity of illumination passes through the diffusion shield and where the harvesting shield is structured to redirect at least a portion of the quantity of illumination from the florescent illumination arrangement toward the diffusion shield; and the florescent illumination arrangement having a set of concentric illumination sources.

Yet another aspect of this application is a method including the steps of providing a quantity of light from a light source; creating a quantity of diffused light by diffusing at least a portion of the quantity of light by passing the at least a portion of the quantity of light though a diffusion shield; providing the quantity of diffused light without direct projection of light from the light source on a component; and observing the component with an imaging system.

Further features of this aspect can include providing the imaging system at a first end of a diffusion shield; providing a manipulation system capable of positioning the component at a second end of the diffusion shield; and harvesting at least a portion of the quantity of light from the light source with a harvesting shield where the harvesting shield is structured to redirect the at least a portion of the quantity of light from the light source toward the diffusion shield. Another feature of this aspect can include the quantity of diffused light being substantially continuous.

While the invention has been illustrated and described in detail in the drawings and foregoing description, the same is to be considered as illustrative and not restrictive in character, it being understood that only the preferred embodiments have been shown and described and that all changes and modifications that come within the spirit of the inventions are desired to be protected. It should be understood that while the use of words such as preferable, preferably, preferred or more preferred utilized in the description above indicate that the feature so described may be more desirable, it nonetheless may not be necessary and embodiments lacking the same may be contemplated as within the scope of the invention, the scope being defined by the claims that follow. In reading the claims, it is intended that when words such as "a," "an," "at least one," or "at least one portion" are used there is no intention to limit the claim to only one item unless specifically stated to the contrary in the claim. When the language "at least a portion" and/or "a portion" is used the item can include a portion and/or the entire item unless specifically stated to the contrary.

What is claimed is:

1. An apparatus comprising:
   first and second concentric light sources capable of providing a quantity of light; the first light source being disposed on a larger radius than the second light source: and
   a diffusion shield structured to diffuse the quantity of light and produce a diffused illumination, said diffused illumination being provided to a component positioned in an interior portion of the diffusion shield.

2. The apparatus of claim 1, further including a support structure wherein the diffusion shield is mechanically coupled with the support structure at a first base portion of the diffusion shield, and wherein the first and second concentric light sources are mechanically coupled with the support structure and positioned radially outward from the first base portion of the diffusion shield.

3. The apparatus of claim 1 further including a harvesting shield wherein the harvesting shield is mechanically coupled with the support structure and positioned radially outward from the first and second concentric light sources; and wherein the harvesting shield redirects at least a portion of the quantity of light from the first and second concentric light sources towards the diffusion shield.

4. The apparatus of claim 2, furthering including an imaging system positioned at the first base portion of the diffusion shield and is capable of producing at least one image of the component.

5. The apparatus of claim 4, further including a manipulation system capable of presenting the component to the imaging system within the diffusion shield and wherein the manipulation system is positioned approximate a second base portion of the diffusion shield.

6. An apparatus comprising:
   a florescent illumination arrangement; and
   a system of shields wherein an object is substantially uniformly illuminated by the florescent illumination arrangement and the system of shields,
   wherein the system of shields further includes a diffusion shield and a harvesting Shield,
   wherein the harvesting shield is structured to redirect at least a portion of the quantity of illumination from the florescent illumination arrangement toward the diffusion shield.

7. The apparatus of claim 6, further including a quantity of illumination from the florescent illumination arrangement being diffused by the system of shields to produce a diffused quantity of illumination wherein the object is substantially uniformly illuminated by the diffused quantity of illumination.

8. The apparatus of claim 6, wherein the diffusion shield is structured to diffuse the quantity of illumination from the florescent illumination arrangement as the quantity of illumination passes through the diffusion shield.

9. The apparatus of claim 6, wherein the florescent illumination arrangement further includes a set of concentric illumination sources.

10. The apparatus of claim 6, furthering including an imaging system positioned at a first base portion of the diffusion shield and is capable of producing at least one image of the object.

11. The apparatus of claim 10, further including a manipulation system capable of presenting the object to the imaging system within the diffusion shield and wherein the manipulation system is positioned approximate a second base portion of the diffusion shield.

12. A method comprising:
   providing a quantity of light from a light source;
   creating a quantity of diffused light by diffusing at least a portion of the quantity of light by passing the at least a portion of the quantity of light through a diffusion shield;
   providing the quantity of diffused light without direct projection of light from the light source on a component; and
   observing the component with an imaging system;
   further including providing a manipulation system capable of positioning the component at a second end of the diffusion shield.

13. The method of claim 12, further including providing the imaging system at a first end of a diffusion shield.

14. The method of claim 12, further including harvesting at least a portion of the quantity of light from the light source with a harvesting shield wherein the harvesting shield is structured to redirect the at least a portion of the quantity of light from the light source toward the diffusion shield.

15. The method of claim 12, wherein the quantity of diffused light is substantially continuous.

* * * * *